United States Patent
Noordam et al.

(10) Patent No.: US 10,786,000 B2
(45) Date of Patent: Sep. 29, 2020

(54) PROCESS TO PRODUCE A YEAST-DERIVED PRODUCT COMPRISING REDUCING SUGAR

(75) Inventors: Bertus Noordam, Echt (NL); Peter Philip Lankhorst, Echt (NL)

(73) Assignee: DSM IP ASSESTS B.V., Heerlen (NL)

( * ) Notice: Subject to any disclaimer, the term of this patent is extended or adjusted under 35 U.S.C. 154(b) by 420 days.

(21) Appl. No.: 14/119,737

(22) PCT Filed: May 15, 2012

(86) PCT No.: PCT/EP2012/058982
§ 371 (c)(1),
(2), (4) Date: Dec. 20, 2013

(87) PCT Pub. No.: WO2012/163668
PCT Pub. Date: Dec. 6, 2012

(65) Prior Publication Data
US 2014/0099402 A1   Apr. 10, 2014

(30) Foreign Application Priority Data
May 31, 2011 (EP) .................................. 11168283

(51) Int. Cl.
| C12N 9/60 | (2006.01) |
| A23L 27/21 | (2016.01) |
| A23L 27/26 | (2016.01) |
| A23L 27/24 | (2016.01) |
| A23L 29/30 | (2016.01) |
| A23L 31/10 | (2016.01) |
| C12N 9/24 | (2006.01) |
| A23L 33/145 | (2016.01) |
| A23L 33/14 | (2016.01) |

(52) U.S. Cl.
CPC ............. *A23L 27/215* (2016.08); *A23L 27/24* (2016.08); *A23L 27/26* (2016.08); *A23L 29/30* (2016.08); *A23L 31/10* (2016.08); *A23L 33/14* (2016.08); *A23L 33/145* (2016.08); *C12N 9/2405* (2013.01); *C12N 9/60* (2013.01); *C12Y 302/01003* (2013.01); *C12Y 302/01028* (2013.01); *C12Y 304/21014* (2013.01)

(58) Field of Classification Search
CPC .................. A23L 1/3018; A23L 1/30
USPC .................................. 426/60, 655, 418, 650
See application file for complete search history.

(56) References Cited

U.S. PATENT DOCUMENTS

| 5,288,509 | A | * | 2/1994 | Potman | .................... C12N 1/06 426/60 |
| 6,159,724 | A | | 12/2000 | Ehret | |
| 2008/0317904 | A1 | | 12/2008 | Kortes et al. | |
| 2012/0114797 | A1 | * | 5/2012 | Perkins | ................ C12N 9/2437 426/48 |

FOREIGN PATENT DOCUMENTS

| EP | 0191513 | * | 1/1986 | ............... A23L 1/23 |
| EP | 0191513 | | 8/1986 | |
| EP | 0806144 | | 11/1997 | |
| JP | 61-185164 A | | 8/1986 | |
| JP | 2001-233817 A | | 8/2001 | |
| JP | 2010532981 A | | 10/2010 | |
| JP | 2010-252643 A | | 11/2010 | |
| WO | 9818342 | | 5/1998 | |
| WO | 2007073945 | | 7/2007 | |
| WO | WO073945 | * | 7/2007 | ............... A23J 3/34 |
| WO | 2010/110998 A1 | | 9/2010 | |
| WO | 2010108542 | | 9/2010 | |

OTHER PUBLICATIONS

Parrou, J. L. et al. Anal. Biochem. 1997. 248: 186-188.*
Chae, H. J. et al. Bioresource Technol. 76: 253-258 (2001).*
International Search Report for PCT/EP2012/058982 dated Jun. 13, 2012.
Mottram, "Flavour Formation in Meat and Meat Products: A Review," Food Chemistry, vol. 62, No. 4, pp. 415-424, (1998).

* cited by examiner

*Primary Examiner* — Hamid R Badr
(74) *Attorney, Agent, or Firm* — McBee Moore Woodward & Vanik IP, LLC

(57) ABSTRACT

Provided is a process to produce a yeast-derived product as well as a yeast autolysate or yeast extract comprising at least 1% w/w reducing sugar based on the total dry matter weight of the yeast extract or yeast autolysate. Also provided is a process to produce a reaction flavour. The yeast extract or yeast autolysate is very suitable for the production of a reaction flavour.

17 Claims, No Drawings

US 10,786,000 B2

PROCESS TO PRODUCE A YEAST-DERIVED PRODUCT COMPRISING REDUCING SUGAR

FIELD OF THE INVENTION

This invention relates to a process to produce a yeast-derived product as well as a yeast autolysate or yeast extract comprising at least 1% w/w reducing sugar based on the total dry matter weight of the yeast extract or yeast autolysate. The invention also relates to a process to produce a reaction flavour.

BACKGROUND OF THE INVENTION

The production of reaction flavours is the result of the Maillard reaction between amino acids and reducing sugars. This reaction, its products and their influence on the taste of food have been the subject of several studies (Motram D. S., (1998) Food Chemistry, 62, pp. 415-424, "Flavour formation in meat and meat products: a review" and references therein; Schrödter, R., Schliemann, R., Woelm, G., (1988) Tech. Charact. Prod. Appl. Food Flavours, pp. 107-114, "Study on the effect of fat in meat flavour formation").

One well-known method to produce reaction flavours is by using a yeast-derived product, e.g. a yeast extract or autolysate. However, in order for the Maillard reaction to take place the addition of a reducing sugar, such as glucose, is often required. However, adding glucose to a yeast-derived products before the Maillard reaction forms a disadvantage because it constitutes an extra processing step which is considered inconvenient. Moreover, adding a non-yeast derived product in the process to make a reaction process is often conceived as not natural by customers, and is therefore undesired. It is an aim of the invention to provide a yeast-derived product such as a yeast extract or autolysate comprising reducing sugars which are derived from the oligo- and polysaccharides that are normally present in the yeast cell used for making the yeast-derived product. These oligo- and polysaccharides are for instance trehalose which is found in the cytosol, glycogen as well as various glucans which are found predominantly in the yeast cell walls. It is another aim of the invention to provide a process to produce a reaction flavour from a yeast-derived product whereby no or only a few little additional components are added.

DESCRIPTION OF THE INVENTION

In a first aspect the invention provides a process to produce a yeast-derived product, comprising (a) contacting a suspension comprising yeast cells with an endoprotease to hydrolyze the yeast protein and (b) contacting the preparation obtained in step (a) with one or more enzymes selected from the group consisting of α-α-trehalase (EC 3.2.1.28), glucoamylase (EC 3.2.1.3), endo-glucanases and exo-glucanases.

The endo-glucanase may be selected from the group consisting of endo-1,3-β-glucanase (EC 3.2.1.39), licheninase (EC 3.2.1.73), endo-1,6-β-glucanase (EC 3.2.1.75) and endo-1,3(4)-β-glucanase (EC 3.2.1.6). The exo-glucanase may be selected from the group consisting of glucan 1,3-β-glucosidase (EC 3.2.1.58), glucan 1,6-β-glucosidase and β-glucosidase (EC 3.2.1.21).

The following enzymes and combinations are highly preferred embodiments of the enzymes used in step (b) of the process of the present invention:
(1) α-α-trehalase (EC 3.2.1.28)
(2) α-α-trehalase (EC 3.2.1.28) and glucoamylase (EC 3.2.1.3)
(3) α-α-trehalase (EC 3.2.1.28) and one or more enzymes selected from the group consisting of endo-glucanase and exo-glucanase
(4) α-α-trehalase (EC 3.2.1.28) and one or more enzymes selected from the group consisting of endo-glucanases.
(5) α-α-trehalase (EC 3.2.1.28) and one or more enzymes selected from the group consisting of exo-glucanases.
(6) α-α-trehalase (EC 3.2.1.28) and glucoamylase (EC 3.2.1.3) and one or more enzymes selected from the group consisting endo-glucanase and exo-glucanase
(7) α-α-trehalase (EC 3.2.1.28) and glucoamylase (EC 3.2.1.3) and one or more enzymes selected from the group consisting of endo-glucanases,
(8) α-α-trehalase (EC 3.2.1.28) and glucoamylase (EC 3.2.1.3) and one or more enzymes selected from the group consisting of exo-glucanases.
(9) α-α-trehalase (EC 3.2.1.28) and endo-1,3-β-glucanase (EC 3.2.1.39)
(10) α-α-trehalase (EC 3.2.1.28) and glucoamylase (EC 3.2.1.3) and endo-1,3-β-glucanase (EC 3.2.1.39)
(11) α-α-trehalase (EC 3.2.1.28) and endo-1,6-β-glucanase (EC 3.2.1.75)
(12) α-α-trehalase (EC 3.2.1.28) and glucoamylase (EC 3.2.1.3) and endo-1,6-β-glucanase (EC 3.2.1.75)
(13) α-α-trehalase (EC 3.2.1.28) and endo-1,3(4)-β-glucanase (EC 3.2.1.6)
(14) α-α-trehalase (EC 3.2.1.28) and glucoamylase (EC 3.2.1.3) and endo-1,3(4)-β-glucanase (EC 3.2.1.6)
(15) any of the above combinations (1) to (14) and one or more enzymes selected from the group consisting of exo-glucanases consisting of glucan 1,3-β-glucosidase (EC 3.2.1.58), glucan 1,6-β-glucosidase and β-glucosidase (EC 3.2.1.21).
(16) any of the above combinations (1) to (14) and glucan 1,3-β-glucosidase (EC 3.2.1.58)
(17) any of the above combinations (1) to (14) and glucan 1,6-β-glucosidase
(18) any of the above combinations (1) to (14) and β-glucosidase (EC 3.2.1.21).

In a preferred embodiment the yeast-derived product that is produced by the process of the first aspect of the invention is a yeast autolysate. In the context of the present invention a "yeast autolysate" is defined, according to the Food Chemical Codex as "the concentrated, nonextracted, partially soluble digest obtained from food-grade yeast. Solubilization is accomplished by enzyme hydrolysis or autolysis of yeast cells. Food-grade salts and enzymes may be added. Yeast, autolyzed, contains both soluble and insoluble components derived from the whole yeast cell. It is composed primarily of amino acids, peptides, carbohydrates, fats, and salts".

In another preferred embodiment the yeast-derived product of the process of the first aspect of the invention is a yeast extract. In the context of the present invention a "yeast extract" is defined, according to the Food Chemical Codex, as follows: "Yeast Extract comprises the water soluble components of the yeast cell, the composition of which is primarily amino-acids, peptides, carbohydrates and salts. Yeast extract is produced through the hydrolysis of peptide bonds by the naturally occurring enzymes present in edible yeast or by the addition of food-grade enzymes.

In an embodiment the process of the first aspect of the invention further comprises subjecting the yeast derived product to a solid-liquid separation step and removing insoluble matter. Subjecting the yeast derived product (i.e.

the contacted solution obtained to a solid-liquid separation step and removing insoluble matter may advantageously result in a yeast-derived product being more soluble, clearer, and/or lower in colour, which may be useful in certain applications where these properties are desired. A yeast-derived product from which insolubles are removed may be referred to as an extract; i.e. it may be regarded as the soluble fraction of said yeast-derived product.

We have surprisingly found that with the process of the first aspect of the invention a yeast-derived product may be produced that is rich in reducing sugars. Preferably, the reducing sugar is glucose. The advantage of the process of the present invention is that the yeast-derived product, such as a yeast autolysate or yeast extract, may comprise sufficient amounts of a reducing sugar, such as glucose, allowing the direct use of the yeast-derived product to make processed flavors thereof without the addition of external reducing sugar such as glucose.

The yeast in the suspension comprising yeast of the process of the first aspect of the invention may be from any type of food-grade yeast, for example baker's yeast, beer yeast or wine yeast. Preferably, the yeast is belonging to the genera *Saccharomyces, Kluyveromyces, Candida* or *Torula*, more preferably to genus *Saccharomyces*, i.e. *Saccharomyces cerevisiae*.

The suspension of yeast cells may be a fermentation broth, but is preferably a cream yeast. Cream yeast is well known in the art, such as the baking industry, and refers to a suspension of yeast cells, obtained from a fermentation broth, optionally washed, with a total yeast dry matter content between 18 and 24%.

In an embodiment, the process of the first aspect of the invention further comprises drying the contacted suspension or extract. This may result in a stable yeast-derived product, e.g. during storage, and which may be lighter in weight, which may be more economical during transport.

The process of the first aspect of the invention may advantageously result in a high yield of dissolved dry matter (% w/w), expressed as the amount (in dry matter weight) of dissolved material in the yeast extract or yeast autolysate, preferably in the yeast extract, as compared to the total dry matter weight of the suspension of yeast cells. Said yield is preferably higher than 70%, more preferably higher than 75%, higher than 80%, even more preferably higher than 85%, most preferably higher than 90%.

In a preferred embodiment, the process of the first aspect of the invention further comprises reducing the amount of free asparagine present in the yeast derived product. Preferably, the amount of free asparagines is reduced by an enzyme capable of reducing the amount of free asparagine such as asparaginase for which the conditions have for example been disclosed in WO2007/073945.

A yeast derived product with reduced amounts of free asparagine is in particular advantageous for applications in which the yeast derived product such as a yeast extract or yeast autolysate is heated, for example when used to produce a reaction flavour, but also when the yeast extract or yeast autolysate is added to food in preparation which is heated before consumption. For example, if yeast derived product such as a yeast extract or yeast autolysate obtained with the process of the first aspect of the invention, having the stated amounts of reducing sugar, is added to soup, crips or chips, or snacks, which are boiled, cooked, or baked, the reduced amounts of asparagine may reduce the formation of acrylamide, the presence of which in food is highly undesired.

The risk of formation of acrylamide may be less with yeast extracts or yeast autolysates known in the art since they contain less glucose.

In a second aspect the invention provides a yeast derived product, obtainable by the process of the first aspect of the invention, comprising at least 1% w/w reducing sugar based on total dry matter weight and whereby the reducing sugar is derived from the oligo- and polysaccharides that are normally present in the yeast cell used for making the yeast-derived product. Preferably the amount of reducing sugar of the yeast derived product is at least 1.5% w/w, more preferably at least 2% w/w, 3% w/w, 4% w/w, even more preferably at least 5% w/w, 6% w/w, 7%, w/w, even more preferably at least 8% w/w, 9%, 10% w/w, 11% w/w, most preferably at least 12% w/w based on the total dry matter weight of the yeast derived product. Depending on the oligo- and polysaccharide content of the yeast, the amount of reducing sugar of the yeast derived product may be as high as 30%, preferably less such as 25% or less or 20% or less. For instance, the yeast may contain high levels of trehalose, preferably at least 1% or as high as 30% based on the total dry matter weight of the yeast.

In the context of the invention a reducing sugar is any sugar that, in solution, has an aldehyde or a ketone group. This allows the reducing sugar to act as a reducing agent, for example in the Maillard reaction and/or in a process to produce a reaction flavour, preferably a reaction flavour from a yeast derived product such as a yeast autolysate or a yeast extract. In the Maillard reaction as well as in the process to produce a reaction flavour, a first reaction is the reaction between the reducing sugar and an amino group of, for example, an amino acid. A highly preferred reducing in the context of the invention is glucose. Glucose constitutes a widely accepted food component and is an effective Maillard agent.

The yeast derived product of the second aspect of the invention is preferably suitable to produce a reaction flavour. Preferred embodiments of the present invention are a yeast autolysate or a yeast extract comprising at least 1% w/w reducing sugar based on total dry matter weight and whereby the reducing sugar is derived from the oligo- and polysaccharides that are normally present in the yeast cell used for making the yeast autolysate or a yeast extract. The yeast autolysate or yeast extract of the second aspect of the invention is preferably obtainable by the process according to the first aspect of the invention.

Preferably the amount of reducing sugar of the yeast autolysate or a yeast extract is at least 1.5% w/w, more preferably at least 2% w/w, 3% w/w, 4% w/w, even more preferably at least 5% w/w, 6% w/w, 7%, w/w, even more preferably at least 8% w/w, 9%, 10% w/w, 11% w/w, most preferably at least 12% w/w based on the total dry matter weight of the yeast autolysate or a yeast extract. Depending on the oligo- and polysaccharide content of the yeast, the amount of reducing sugar of the yeast autolysate or yeast extract may be as high as 30%, preferably less such as 25% or less or 20% or less. For instance, the yeast may contain high levels of trehalose, preferably at least 1% or as high as 30% based on the total dry matter weight of the yeast.

A highly preferred reducing sugar in the context of the invention is glucose. Glucose constitutes a widely accepted food component and is an effective Maillard agent.

The yeast extract or yeast autolysate of the second aspect of the invention may advantageously have a dark color, which color may be darker than yeast extracts or yeast autolysates known in the art. Said color may be determined for example by measuring the absorbance, e.g. at 450 nm. If it is desired to further increase the darkness of the yeast extract or yeast autolysate of the second aspect of the invention, it is possible to subject said yeast extract or yeast autolysate to elevated temperature, e.g. between 30 and 100 C.

Preferably the reducing sugar of the yeast extract or yeast autolysate of the second aspect of the invention is glucose. Glucose constitutes a widely accepted food component and is an effective Maillard agent.

In a third aspect of the invention the invention provides a process to produce a reaction flavour comprising as a step (c) incubating the yeast-derived product of the second aspect of the invention and defined therein, under conditions of temperature and water content to obtain a reaction flavour. We have surprisingly found that by the process of the third aspect of the invention a reaction flavour can be produced without the necessity to adding external reducing sugars such as glucose, and which reaction flavour therefore may advantageously be labeled as "natural" or "clean label".

In a preferred embodiment, the process of the third aspect of the invention includes all the steps of the process of the first aspect of the invention. This embodiment optionally includes the solid-liquid separation step and removing insoluble matter in the process of the first aspect of the invention. This step is optional and may therefore be left out when desired. In one embodiment, the process of the third and first aspect of the invention does not include solid-liquid separation step and removing of insoluble matter. This may result in a higher amount of fatty material stemming from the yeast cell walls, which may result in more mouthfeel or additional flavour.

In another embodiment, the process of the third aspect of the invention comprises adding one or more additional components. The additional components may be added to the yeast-derived product obtained by the process of the first aspect of the invention or to the yeast derived product of the second aspect of the invention such as a yeast extract or yeast autolysate. Within the context of the invention water is not considered to be an additional component. Likewise, enzymes used in the process of the first aspect of the invention are not considered to be an additional component.

In a preferred embodiment the additional component is a sulphur-containing component, such as cystein or glutathione. In another preferred embodiment, the additional component is a yeast-derived product. "Yeast-derived" means that the component is obtained from or produced by yeast. An advantage of a yeast-derived additional component is that it is generally regarded as safe and therefore very suitable to produce a food grade reaction product, and that consumers generally do not appreciate a reaction flavour from yeast to which any non-yeast derived components have been added to the final product and/or during the process to produce it.

In another preferred embodiment the one or more additional components is selected from the group consisting of yeast extract, yeast autolysate, cystein, glutathione, free amino acids and a reaction flavour. Preferably, the one or more additional components is a reaction flavour, more preferably a reaction flavour produced from a cystein comprising yeast derived product and/or a glutathione comprising yeast derived product, such as a yeast extract or yeast autolysate, even more preferably a reaction flavour which has been produced in an extruder, as for example described in the Examples of WO2010/037783. Adding a reaction flavour as the one or more additional components may allow to produce a reaction flavour with a specific flavour, such as for example a beef flavour or a roast beef flavour, which flavour may advantageously be concentrated.

The one or more additional components may be added during any stage of the process of the first or third aspect of the invention. It may be added before or after the step (a) of the process of the first aspect of the invention and/or before or after the solid-liquid separation. The one or more additional components may also be added during more than one stage, e.g. before and after step (a), or before step (a) and after the solid-liquid separation, or before and after step (a) and after the solid-liquid separation. The amount of the one or more additional components added is preferably such that the total amount of the one or more additional components in the yeast-derived product obtained by the process of the first aspect of the invention or the yeast extract or yeast autolysate of the second aspect of the invention is between 0.1% w/w and 99% w/w, more preferably between 0.5 and 95%, between 1 and 90%, more preferably between 2 and 80%, between 3 and 70%, between 4 and 60%, most preferably between 5 and 50% w/w based on the total weight of the yeast derived product or yeast extract or yeast autolysate. By varying the amount of the one or more additional components various types of flavours may be obtained. For example, the strength of the flavour, or "sulphuriness" of the flavour may be tuned by varying the amount of the one or more additional components, such that the skilled person can, without undue burden, establish suitable amounts in order to obtain the desired type of flavour. Adding one or more additional components in the process of the third aspect of the invention may allow to improve the efficiency of the Maillard reaction. It may also be advantageous in that it may allow to produce a specific reaction flavour which cannot, or not efficiently, be produced when no additional component is added, such as for example a beef flavour.

The water content of the yeast-derived product of the second aspect of the invention or obtained by the process of the first aspect of the invention is preferably between 1 and 20% w/w based on the total weight of the yeast-derived product or yeast extract or yeast autolysate, more preferably between 1.5 and 10% w/w, even more preferably between 2 and 5% w/w.

The temperature in step (c) of the process of the third aspect of the invention is preferably between 50° C. and 180° C., more preferably between 75° C. and 170° C., even more preferably between 100° C. and 160° C. If the temperature is too high, e.g. more than 180° C., the reaction flavour may burn. At higher temperature, e.g. at 180° C., the reaction time may be shorter than when the temperature is lower, e.g. 50° C. At lower water content, e.g. 2% w/w, the temperature may be higher e.g. 180° C.

The incubation in step (c) may be carried out in equipment that is generally known in the art, such as reaction kettles, (vacuum) ovens, cooking pans and the like. Preferably, step (c) of the process of the third aspect of the invention is carried out in an extruder. The extruder may be any type of extruder suitable for the production of reaction flavours, such as a twin extruder. Extruders, e.g. twin extruders, are known in the art. The extruder may have any volume, the volume being the maximum volume inside the extruder which may be taken by the composition. Preferably the volume is between 1 gram and 1000 kg. More preferably the volume is between 5 grams and 100 kg, more preferably between 10 grams and 10 kg. The yeast-derived product obtained by the process of the first aspect of the invention or the yeast extract or yeast autolysate of the second aspect of the invention, and optionally water and/or oil may be introduced into the extruder through the same or separate feeders. The reaction flavour may leave the extruder at a pressure, outside the extruder, varying from reduced pressure (e.g. 5 mbar) to atmospheric pressure (e.g. approximately 1 bar). The reaction flavour produced by the process of the third aspect of the invention can be further cooled and/or dried using a cooling belt or any other method known in the art. An extruder may be advantageous in that the process according to the third aspect of the invention may be more reproducible and/or stable, e.g. during storage. Using an extruder in step (c) of the process of the third aspect of the invention may also be advantageous since it allows for a continuous process, which may result in a higher yield of reaction flavour. The use of an extruder in step (c) of the process of the third aspect of the invention may be advantageous since higher pressures and or process temperatures may be reached in step (c). Moreover, use of an extruder may be advantageous since it may allow intimate mixing. This may be especially important when one or more additional components is added, particularly when adding a reaction flavour as the one or more additional components. Also, the use of an extruder in step (c) of the process of the third aspect of the invention may be advantageous since it may result in a homogeneous reaction flavour, i.e. a reaction flavour in which the flavour is homogeneously distributed over the product leaving the extruder. Also, the use of an extruder in step (c) of the process of the third aspect of the invention may advantageously result in a reaction flavour which is more concentrated as compared to a reaction flavour produced e.g. by vacuum oven. The use of an extruder in step (c) of the process of the third aspect of the invention may also be advantageous in that the reaction flavour may be free-flowing after milling the extrudate. The use of an extruder in step (c) of the process of the third aspect of the invention may also be advantageous in that it is simple. The use of an extruder in step (c) of the process of the third aspect of the invention may also be advantageous in that it may result in a roast flavour.

The incubation in step (c) of the process of the third step of the invention is preferably done in the presence of an enzyme capable of reducing the amount of free asparagine. Examples of such enzymes are described in WO2007073945, and include asparaginase.

In a fourth aspect the invention provides a reaction flavour obtainable by the process of the third aspect of the invention. The reaction flavour of the third aspect of the invention may have any flavour. The reaction flavour may have a vegetable flavour such as for example cabbages such as cauliflower, broccoli, Brussels sprout, Chinese kale or Chinese broccoli, kale or spring greens, collard greens, kohlrabi, onion, cocoa, chocolate, peanut, roasted peanut, coffee or it may have a meat flavour. Meat flavours include but are not limited to poultry flavours such as flavours of chicken, turkey, pheasant, goose, swan, and duck, or other meat flavours such as the flavours of beef, lamb, sheep, goat, horse, and pork. The reaction flavour may be a boiled, braised, cooked, grilled, roasted, smoked, fried, or broth flavour. Preferably the reaction flavour has a beef flavour. More preferably the reaction flavour has a roast flavour.

Materials and Methods

Glucose and trehalose were determined using HPLC using an Aminex HPX-87G column (BioRad). The retention times of trehalose and glucose were 6.65 and 7.93 minutes respectively.

Protein (i.e. the total mixture of amino acids, peptides and protein) was determined using the Kjeldahl method for total nitrogen using a conversion factor of 6.25.

Filtrase NL® (DSM Food Specialties, the Netherlands) is a non-GMO liquid enzyme product used for improving the viscosity and filterability of beer and comprises an enzyme mixture produced by a selected strain of *Talaromyces emersonii*. The major activity is endo-1,3(4)-β-glucanase (EC 3.2.1.6) but other enzyme activities such as xylanase and trehalase are present as well.

EXAMPLES

Example 1

Production of a Reducing Sugar Containing Yeast Extract

To cream yeast of *Saccharomyces cerevisiae* (20% w/w dry matter) was added 10 mg/g (based on dry matter) *Bacillus licheniformis* endoprotease (Alcalase, Novozymes, Denmark). The conditions of the contacting were: 53° C., pH 6, during 4 hours; followed by 60° C., pH 6, during 2 hours; followed by 53° C., pH 5.3, during 16 hours; followed by 70° C. for 30 min to inactivate the protease. Next, the pH was decreased to pH 4.5 and the temperature was decreased to 55° C. and 10 mg/g endo-1,3-beta-glucosidase containing enzyme mixture from *Talaromyces* (Filtrase NL®—DSM Food Specialties, the Netherlands), glucoamylase (Bakezyme AG800, DSM Food Specialties, the Netherlands, 1 mg/g) and fungal amylase (DSM Food Specialties, the Netherlands) were added. This contacting was continued for another 6 hours. Subsequently the temperature was lowered to 50° C. and a mixture of beta-glucanase, cellulase, protease, and chitinase was added (Lysing Enzymes from *Trichoderma harzianum*, 1 mg/g dm, Sigma Aldrich) at pH 4.5 for 17.5 hours.

The enzyme mixture from *Talaromyces* also comprised trehalase activity as was demonstrated in a separate experiment by incubating pure trehalose with the enzyme mixture from *Talaromyces* and measure the residual trehalose as well as the glucose formed by HPLC (see Materials and Methods).

A yeast extract (yeast extract A) was obtained by collecting and concentrating the supernatant after centrifugation. A yeast extract powder ("yeast extract A powder") of the yeast extract was made by spray-drying. The total dry matter of the cream yeast is 100% by definition. Results are presented in Table 1.

TABLE 1

| | Results | | | |
|---|---|---|---|---|
| Yeast derived product | Dissolved dry matter (% w/w) | Glucose (% w/w on dissolved d.m.) | Glucose (% w/w on total d.m.) | Protein (% w/w on dissolved d.m.) |
| Cream yeast | 3 | 8 | 0.24 | ND |
| Yeast extract A | 92 | 17 | 16 | ND |
| Yeast extract A powder | 92 | 12 | 11 | 50 |

ND = not determined

Example 2

Production of a Beef-Type Reaction Flavour

A blend was prepared by mixing 28.7 g of the yeast extract powder of Example 1 (yeast extract A powder), 6.9 g of a reaction flavour, and 0.35 grams of high oleic sunflower oil (HOZOL, Brenntag, the Netherlands). The reaction flavour in the blend was prepared by extrusion as described in the Examples of WO2010/037783, for the exact composition and conditions see Table 2. The ratio of yeast extract powder:reaction flavour:high oleic sunflower oil in the blend was 79:20:1. The blend was subsequently heated at 125° C. for three minutes in a twin-screw extruder at a screw speed of 100 rpm. After cooling to room temperature, the extrudate (reaction flavour) was milled to a fine dark brown powder and stored in a plastic jar. The reaction flavour was evaluated by a trained expert panel.

TABLE 2

| Composition | |
|---|---|
| Residence time | 1 minute |
| Temperature of the composition | 180° C. |
| Gistex ® LS powder (DSM Food Specialties-The Netherlands) | 10% w/w dm |
| Yeast extract containing 15% w/w glutathione (based on dry matter) | 89% w/w dm |
| HOZOL | 1.0% w/w dm |

Five reaction flavours were made by varying the ratio of yeast extract powder to reaction flavour in the blend (the amount of sunflower oils in the blend was always 1%) according to Table 3.

TABLE 3

| Reaction flavours | |
|---|---|
| Reaction flavour | Ratio yeast extract powder:reaction flavour in the blend |
| Reaction flavour 1 | 80:20 |
| Reaction flavour 2 | 82.5:17.5 |
| Reaction flavour 3 | 85:15 |
| Reaction flavour 4 | 87.5:12.5 |
| Reaction flavour 5 | 90:10 |

The five reaction flavours differed in sensory profile, but were always beef-like. The reaction flavours made with more reaction flavour in the blend were more sulphury and more intense.

Example 3

A blend was prepared by mixing 31.5 g of the yeast extract powder of Example 1 (glucose level 12%), 3.1 grams of Maxarome®Plus (a yeast extract from *Saccharomyces cerevisiae* obtainable from DSM Food Specialties, Delft, the Netherlands) and 0.35 grams of high oleic sunflower oil (HOZOL). The ratio of yeast extract powder:Maxarome®Plus:high oleic sunflower oil was 90:9:1. The blend was subsequently heated at 140° C. for 3 minutes in a twin-screw extruder at a screw speed of 150 rpm. After cooling to room temperature, the extrudate (reaction flavour) was milled to a fine dark brown powder and stored in a plastic jar. The reaction flavour had a roast meat flavour.

Example 4

Yeast extract B was produced according to the procedure of Example 1. As in Example 1, a powder was made by spray-drying. The dry weight content was 97.3% and the protein content was 50.1% w/w; based on Kjehldahl nitrogen which was 8% w/w.

Approximately 10-20 mg of sprayed-dried yeast extract B or a Comparative yeast extract (Gistex® LS powder, available from DSM Food Specialties, the Netherlands) was dissolved in 1 ml of $D_2O$. Gistex® LS powder is a standard commercial yeast extract which is made by a process including treatment of a cream yeast with Alcalase, a *Bacillus endoprotease* available from Novozymes, Denmark, but which process does not include treatment with endo-1,3-beta-glucosidase, glucoamylase, fungal amylase, beta-glucanase, cellulase, and/or chitinase.

Maleic acid di-sodium salt or fumaric acid di-sodium salt were added as internal standard. NMR spectra were recorded on a Bruker Avance III operating at 600 MHz and equipped with a 5 mm cryo-probe.

The NMR spectra showed that yeast extract B was enriched in glucose as compared to the comparative yeast extract and does not contain trehalose. The data suggest that the trehalose, normally present in yeast extract, is converted by the trehalase activity present in the enzyme mixture from *Talaromyces* (Example 1) to glucose.

TABLE 4

| Composition of yeast extracts (% based on dry matter) | | |
|---|---|---|
| | Comparative yeast extract | yeast extract B |
| Protein | 65% | 50.1% |
| Glucose | 0% | 8.9% |
| Trehalose | 5.5% | 0% |

Example 5

A cream yeast of *Saccharomyces cerevisiae* (20% w/w dry matter) was subjected to a heat shock for 5 minutes at 60° C. Then, 10 mg/g (based on dry matter) *Bacillus licheniformis* endoprotease (Alcalase, Novozymes, Denmark) was added. The conditions of the contacting were: 60° C., pH 6, during 4 hours; followed by 51.5° C., pH 5.1, during 16 hours.

Next, the pH was decreased to pH 4.5 and the temperature was decreased to 50° C. and 10 mg/g endo-1,3-beta-glucosidase containing enzyme mixture from *Talaromyces* (Filtrase NL®—DSM Food Specialties, the Netherlands) was added and incubated for 18 hours. As a final step, the mixture was heat shocked at 65° C. for 1 hour at pH 4.5. The results are shown in Table 5.

TABLE 5

| Composition of yeast derived products (% based on dry matter) | | |
|---|---|---|
| Treatment | Trehalose content % of total dry matter | glucose content % of total dry matter |
| After protease treatment | 9.1% | 0.6% |
| After incubation with the enzyme mixture from Talaromyces | 3.0% | 11.4% |

The invention claimed is:
1. A process for producing a yeast-derived product comprising at least 5% w/w of a reducing sugar comprising:
   a. contacting a suspension comprising a yeast cell with an endoprotease to hydrolyze yeast protein to form a preparation;
   b. contacting the preparation with an enzyme mixture produced by a *Talaromyces emersonii* strain compris- ing α-α-trehalase (EC 3.2.1.28), endo-1,3(4)-β-glucanase (EC 3.2.1.6) and glucan 1,3-β-glucosidase (EC 3.2.1.58)

wherein said process does not comprise addition of external reducing sugar and wherein said yeast-derived product is a yeast autolysate and/or a yeast extract.

2. The process according to claim 1, wherein said preparation is further contacted with glucoamylase (EC 3.2.1.3) and/or fungal amylase.

3. The process according to claim 1, wherein said preparation is further contacted with an endo-glucanase selected from the group consisting of endo-1,3-β-glucanase (EC 3.2.1.39), and endo-1,6-β-glucanase (EC 3.2.1.75).

4. The process according to claim 1, wherein said preparation is further contacted with glucan 1,6-β-glucosidase.

5. The process according to claim 1, further comprising subjecting said yeast derived product to solid-liquid separation and removing insoluble matter.

6. The process according to claim 1, wherein said yeast-derived product is a yeast autolysate.

7. The process according to claim 1, wherein said yeast-derived product is a yeast extract.

8. The process according to claim 5, further comprising drying said yeast-derived product.

9. A yeast-derived product, obtained by the process of claim 1, comprising at least 5% w/w reducing sugar based on total dry matter weight, wherein said reducing sugar is derived only from the oligo- and polysaccharides that are present in the yeast cell used for making said yeast-derived product during the process, wherein said yeast-derived product is a yeast autolysate and/or a yeast extract.

10. The yeast-derived product according to claim 9, wherein said reducing sugar is glucose.

11. A process for producing a reaction flavour comprising incubating a yeast-derived product as defined in claim 9, under conditions of temperature and water content to in order to obtain a reaction flavour.

12. The process according to claim 11, comprising adding at least one additional component.

13. The process according to claim 12, wherein said at least one additional component is yeast-derived.

14. The process according to claim 12, wherein said at least one additional component is a reaction flavour.

15. The process according to claim 11, whereby the incubating is carried out in an extruder.

16. A reaction flavour obtained by the process according to claim 11.

17. The process according to claim 1, further comprising:
c. contacting the preparation obtained in b) with one or more of the following: beta-glucanase, cellulase, protease, and chitanase.

* * * * *